United States Patent [19]
Kunik

[11] Patent Number: 6,062,001
[45] Date of Patent: May 16, 2000

[54] SHARPS DISPOSAL CONTAINER

[75] Inventor: Burton J. Kunik, Houston, Tex.

[73] Assignee: Sharps Compliance, Inc., Houston, Tex.

[21] Appl. No.: 09/365,574

[22] Filed: Aug. 2, 1999

[51] Int. Cl.[7] .................................................. B65D 85/24
[52] U.S. Cl. ........................... 53/468; 206/366; 220/254; 220/326
[58] Field of Search ............................... 53/468; 206/366, 206/370; 220/254, 326, 796, 797, 799, 805, 908.1, 908.3; 604/192, 197, 198

[56] References Cited

U.S. PATENT DOCUMENTS

| | | |
|---|---|---|
| 4,715,498 | 12/1987 | Hanifl . |
| 4,779,728 | 10/1988 | Hamifl . |
| 4,804,090 | 2/1989 | Schuh et al. . |
| 4,874,103 | 10/1989 | Quisenberry et al. .................. 220/254 |
| 5,145,063 | 9/1992 | Lee . |
| 5,249,680 | 10/1993 | Shillington .............................. 206/366 |
| 5,387,735 | 2/1995 | Ponsi et al. . |
| 5,402,887 | 4/1995 | Shillington .............................. 206/366 |
| 5,409,112 | 4/1995 | Sagstetter ................................ 206/366 |
| 5,409,113 | 4/1995 | Richardson et al. ..................... 206/366 |
| 5,413,243 | 5/1995 | Bemis et al. . |
| 5,495,941 | 3/1996 | Leonard ................................... 206/366 |
| 5,570,783 | 11/1996 | Thorne et al. ........................... 206/366 |
| 5,577,779 | 11/1996 | Dangel .................................... 220/326 |
| 5,603,404 | 2/1997 | Nazare et al. . |
| 5,630,506 | 5/1997 | Thorne et al. ........................... 206/366 |
| 5,690,242 | 11/1997 | Campbell, Jr. . |
| 5,740,909 | 4/1998 | Nazare et al. . |
| 5,772,059 | 6/1998 | McCord . |
| 5,791,471 | 8/1998 | Radmand . |

*Primary Examiner*—Jim Foster
*Attorney, Agent, or Firm*—Kuffner & Associates

[57] ABSTRACT

A disposable container for safe disposal of used pen syringe needles includes a plurality of walls defining a receptacle for receiving used needles therein. The container is provided with an axially extending passage through which needles are deposited within the container. The axial passage is formed by a downwardly extending truncated cone integrally formed with the cover of the container. The truncated cone includes gripping means for holding a needle for depositing into the container. A cap member pivotally connected to the cover of the container includes a plunger which upon closure of the cap member extends through the axial passage forcing the needle held by the gripping means into the container. When the container is not in use, the cap member seals the open axial passage and is maintained in locking engagement with the container.

10 Claims, 4 Drawing Sheets

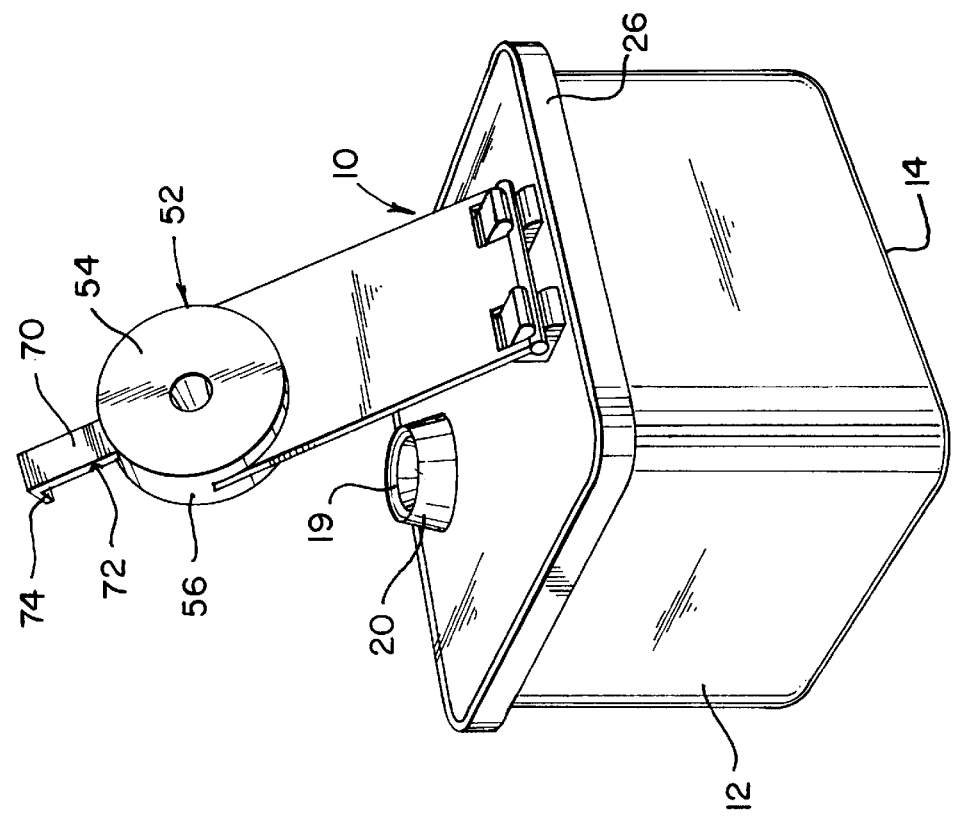
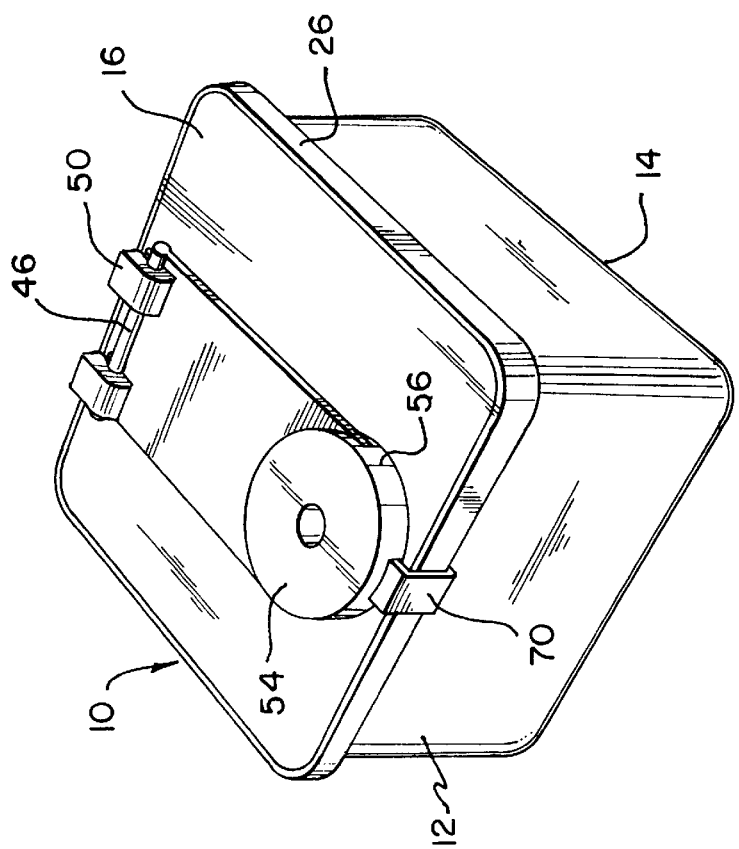

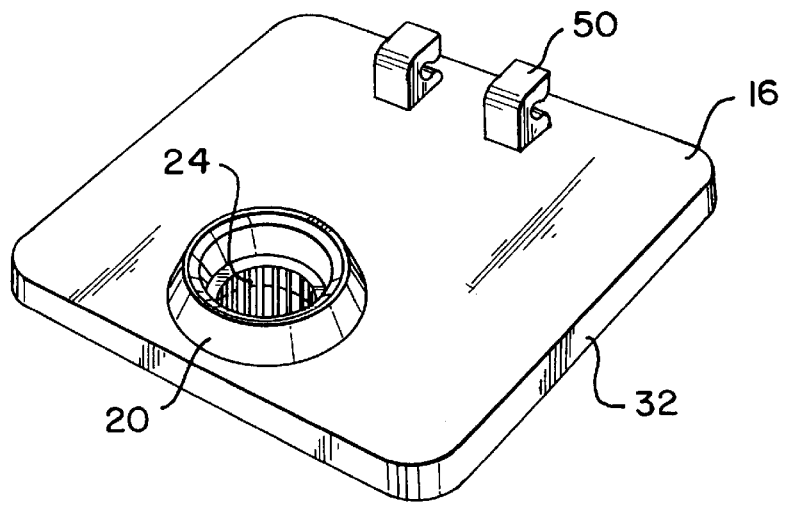
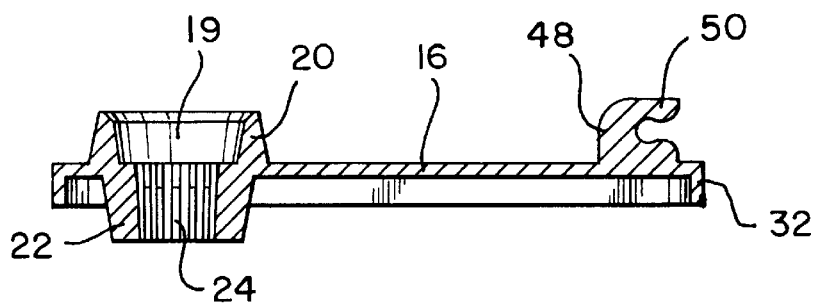
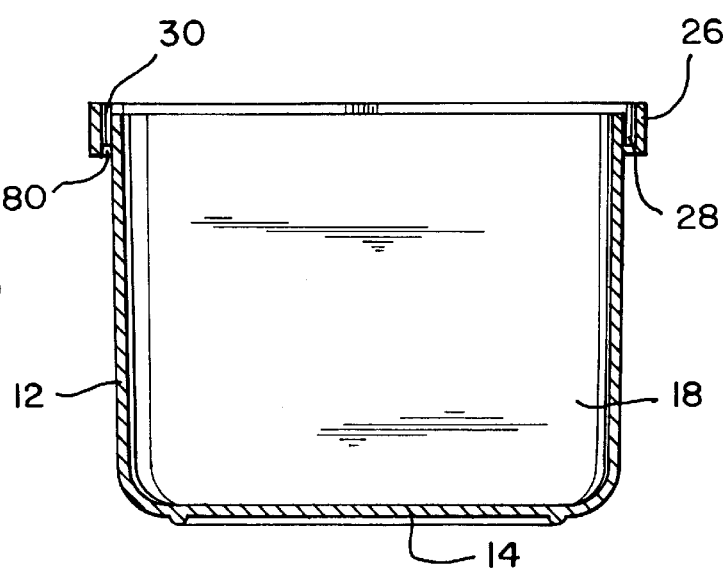

SHARPS DISPOSAL CONTAINER

BACKGROUND OF THE INVENTION

The present invention generally relates to containers for safely disposing used medical instruments and, more particularly, to a sharps disposal container for disposing of pen syringe needles.

Disposal of sharps such as surgical knives, blades, hypodermic needles and the like is a tremendous problem for hospitals and other healthcare facilities. Used sharps may become contaminated by body fluids and the like creating a hazard for anyone that may handle them following their use. Hospitals have developed stringent policy procedures for the safe disposal of used sharps, such as requiring sharps disposal containers in the emergency and examining rooms, and each patient room. Because of their potentially dangerous nature, particularly with present concerns regarding accidental transmittal of infectious diseases and syringe reuse, typical sharps disposal containers are designed not only to permit disposal but also to prevent unintentional contact with or theft of any object deposited in the disposal container.

The present growing trend of providing home healthcare, tremendously increases the potential for inadvertent handling of used sharps, particularly of pen syringe needles. Medical care provided in the patient's home exposes not only the patient but also other individuals without medical experience to the inherent dangers of used needles. Existing sharps disposal containers typically include closure devices which permit sharps, such as needles, to be placed within the container. Many of these sharps disposal containers include a permanent closure device also used as a temporary cover until the container is filled and ready for permanent closure. This often results in the unintentional permanent closure of the container before it is completely filled. The partially filled container must nonetheless be destroyed, and thereby resulting in the waste of containers and added cost to the hospital and patient.

Many patients must administer multiple doses of medication daily. A pen syringe is particularly suitable for administering such multiple doses. The patient must therefore safely dispose many needles. There is a need therefore for a container for disposing pen syringe needles, which container may be economically manufactured while providing an adequate level of safety to the user, and yet preventing unintentional permanent closure of the container.

SUMMARY OF THE INVENTION

In accordance with the present invention, a disposable sharps disposal container for safely disposing of pen syringe needles includes a plurality of sidewalls, a bottom and a cover defining a receptacle for receiving used needles therein. The container is provided with an axial passage through which needles may be deposited in the container. The passage is formed by a downwardly extending truncated cone integrally formed with the cover of the container. The truncated cone includes gripping means for holding a needle to be dropped into the container. A cap member pivotally connected to the cover of the container includes a downwardly extending plunger which upon closure of the cap member is received through the axial passage for forcing a needle held by the gripping means into the container. When the container is not in use, the cap member seals the open passage and is maintained in locking engagement with the container.

BRIEF DESCRIPTION OF THE DRAWINGS

So that the manner in which the above recited features, advantages and objects of the present invention are attained can be understood in detail, a more particular description of the invention, briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 1 is a perspective view of a sharps disposal container in accordance with the present invention depicting the container in a closed position;

FIG. 2 is a perspective view of the sharps disposal container of the present invention illustrating the container in an open position;

FIG. 3 is a perspective view of the top cover of the sharps disposal container of the present invention;

FIG. 4 is a section view of the sharps disposal container of the present invention taken along line 4—4 of FIG. 3;

FIG. 5 is a section view of the sharps disposal container of the present invention;

DETAILED DESCRIPTION OF A PREFERRED EMBODIMENT

Figure 7:
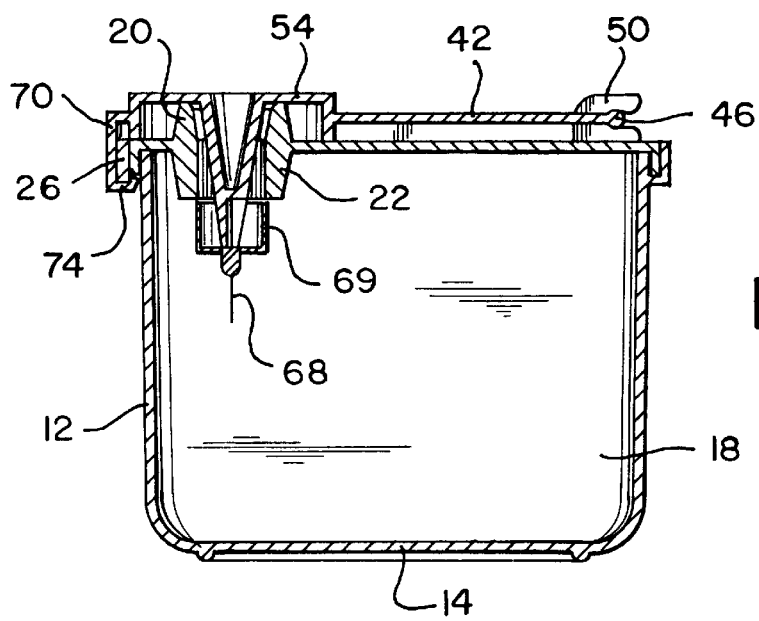
FIG. 7 is a section view of the sharps disposal container of the present invention illustrating a needle being dropped into the container.

Referring first to FIG. 1, a sharps disposal container in accordance with the present invention is generally identified by the reference numeral 10. The container 10, made of a puncture resistant material, includes a container body formed by a plurality of sidewalls 12, a bottom 14 and a top cover 16 which enclose an interior chamber 18, as best shown in FIG. 7. The upper end of the container 10 is provided with a flange 26 extending about the sidewalls 12. The flange 26 is spaced from the sidewalls 12 by a horizontally extending leg member 28 secured to the external surface of the sidewalls 12 proximate the upper ends of the sidewalls 12. The flange 26, leg member 28 and sidewalls 12 cooperate to from an open channel 30 about the upper perimeter of the container 10, as best shown in FIG. 5. The channel 30 is sized to receive a rim 32 integrally formed with the top cover 16. As shown in FIG. 4, the rim 32 extends downwardly about the perimeter of the cover 16. Once assembled, the rim 32 is received in the channel 30 so that the cover 16 is permanently secured to the sidewalls 12 and cannot be separated therefrom.

Referring still to FIG. 4, the cover 16 includes an axial passage 19 extending through the panel 16 and providing access to the receiving chamber 18 for depositing used needles into the container 10. The upper end of the passage 19 is formed by an upstanding cylinder 20 projecting upward from the cover 16 and the lower end thereof is formed by a downwardly extending truncated cone 22 opening into the receiving chamber 18. The internal surface of the cone 22 includes longitudinally extending ridges 24 which form a circumferential gripping surface for firmly gripping a needle or the like inserted into the passage 19.

Figure 6:
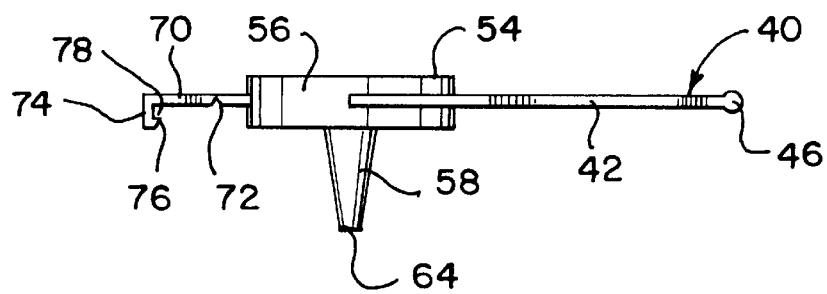
FIG. 6 is a side view of the container cap device of the sharps disposal container of the present invention.

Referring now to FIGS. 2 and 6, the container closure device 40 includes a rigid strap 42 pivotally connected to the cover 16. The strap 42 includes a pair of spaced and aligned openings 44 formed adjacent the distal end of the strap 42. The openings 44 are bounded at one end thereof by pins 46 integrally formed with the strap 42. The pins 46 are received in channel-shaped brackets 48 provided on the cover 16, as best shown in FIG. 3. The brackets 48 include leg members 50 which, upon connecting the strap 42 to the cover 16, extend through the openings 44 so that the pins 46 of the strap 42 are pivotally received by the brackets 48.

The container closure device further includes a cap 52 forming the opposite or proximal end of the strap 42. The cap 52 includes a substantially planar disc 54 having a circumferential lip 56 extending downwardly therefrom. A cone-shaped plunger 58 projects downwardly from the bottom surface of the cap disc 54. The plunger 58 is centrally located on the cap disc 54 and has a vertical axis coincident with the vertical axis of the disc 54.

Figure 8:
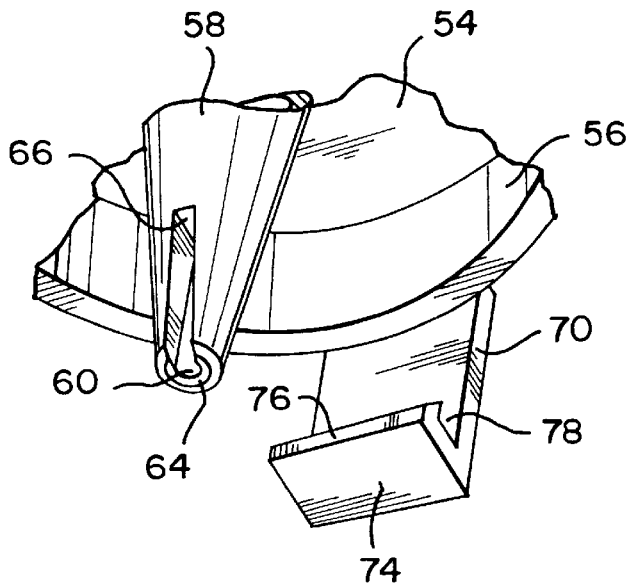
FIG. 8 is an enlarged partial perspective view illustrating the plunger of the sharps disposal container of the invention engaging a needle.
Figure 9:
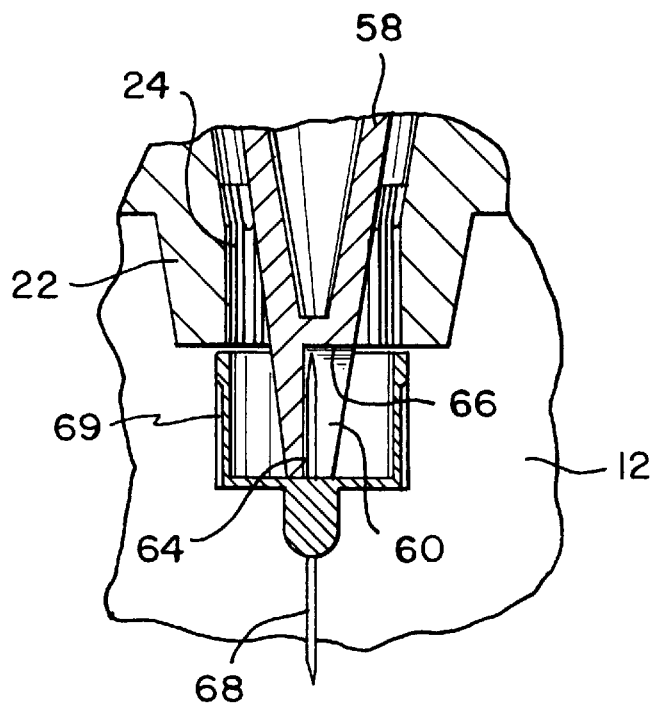
FIG. 9 is an enlarged partial section view illustrating a needle dropping into the sharps disposal container of the invention.

The plunger 58, as more fully shown in FIGS. 8 and 9, includes a channel 60 extending from its distal end 64 and terminating at a transverse shoulder 66 extending horizontally across the plunger 58. The channel 60 provides clearance for the needle 68 on the downstroke of the plunger 58.

Figure 10:
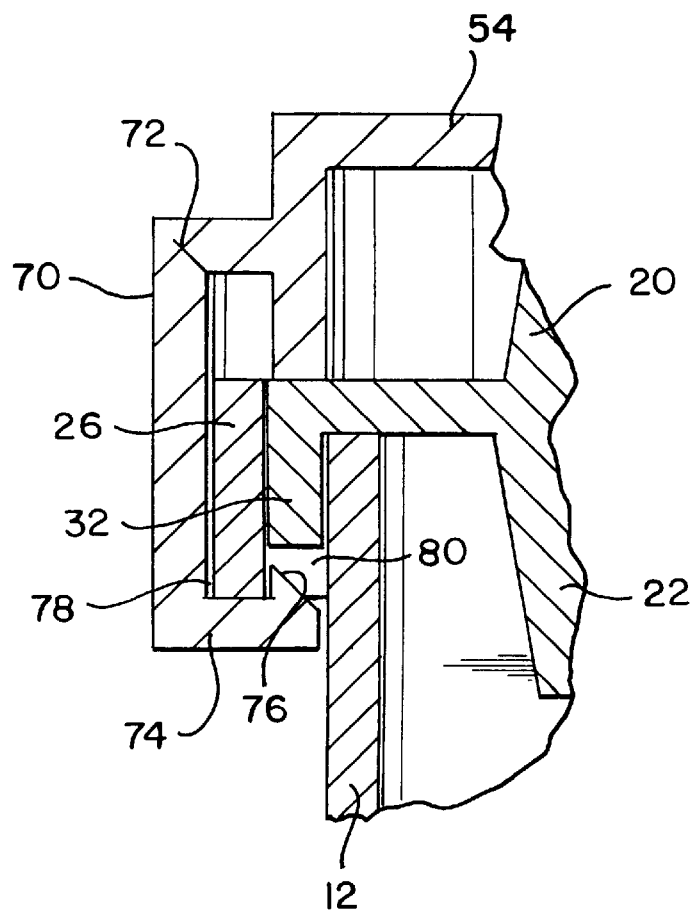
FIG. 10 is an enlarged partial section view illustrating the locking mechanism of the sharps disposal container of the invention.

Referring now to FIGS. 6 and 10, the container closure device 40 further includes a locking tab 70 extending outwardly from the circumferential lip 56 of the container cap 52. The locking tab 70 is secured to the circumferential lip 56 and is in axial alignment with the strap 42. The tab 70 is provided with a notch 72 which appears substantially V-shaped in the side view of FIG. 6. The notch 72 is formed by opposed angularly extending surfaces which extend from the bottom surface of the tab 70 and intersect at a point just below the upper surface of the tab 70. The notch 72 permits the tab 70 to bend downward into the locking position shown in FIG. 10.

Referring now to FIG. 8, a latch member 74 extends perpendicularly from the distal end of the tab 70. The latch member 74 terminates in an upstanding edge 76 which is spaced from and facing the bottom surface of the tab 70. The tab 70, latch member 74 and edge 76 define a channel 78 therebetween. In the locked position shown in FIG. 10, the latch member 74 is in interlocking engagement with the perimeter flange 26 which has a lower edge thereof received in the channel 78. The edge 76 of the latch member 74 extends through a slot 80 formed in the leg member 28 of the perimeter flange 26 and firmly engages the inner surface of the flange 26, thereby retaining the container cap 52 in the closed position shown in FIG. 1.

Referring now to FIGS. 7 and 9, use of the sharps disposal container 10 of the invention will be described in greater detail. The assembled container 10, as noted herein, functions as disposable storage for used needles from a pen syringe, particularly in a home healthcare environment. Preferably, the container 10, including the cover 16 and the closure device 52, are all molded by conventional plastic injection methods. The container 10 is light weight and convenient for home use, and made of puncture resistant materials for safely storing used needles. It is understood however that the container 10 may be made of other suitable materials.

The disposal container 10 is used by first unlatching the latch 74 and withdrawing the plunger 58 from the axial passage 19 extending through the cover 16. The strap 42 and cap 52 are lifted to fully expose the passage 19. The used needle 68 is deposited in the chamber 18 of the container 10 by inserting the needle 68 into the axial passage 19 so that the lower end of the pen syringe barrel (not shown in the drawings) is received in the cylinder 20 and the needle hub 69 is firmly gripped by the gripping surface 24 of the cone 22. The needle 68 is removed from the pen syringe by twisting the syringe barrel to unscrew it from the needle hub 69. The needle hub 69 which is frictionally engaged by the gripping surface 24 of the cone 22 does not rotate when the syringe barrel is twisted. As the pen syringe is twisted, the needle 68 detaches from the syringe barrel while the needle 68 and needle hub 69 are held in the cone 22. The plunger 58 is then inserted into the axial passage 19 and advanced into the cone 22. The upper end of the needle 68 is received in the slot 60 of the plunger 58 as the distal end 64 of the plunger 58 advances into the cone 22 and engages the needle hub 69. As the plunger 58 completes its downstroke, the needle 68 and needle hub 69 are forced past the gripping surface 24 and drop into the chamber 18 of the container 10. The cap 52 is locked in the closed position by interlocking the latch 74 with the perimeter flange 26 of the container 10. In the locked position, the cap 52 completely encloses the open passage 19. The bottom of the disc 54 seats against the top edge of the cylinder 20 and the lip 56 seats against the cover 16 so that the passage 19 is completely sealed. Redundant sealing is provided by the plunger 58 which, in the fully closed position, is in sealing engagement with the gripping surface 24 of the cone 22.

The foregoing disclosure and description of the invention are illustrative and explanatory thereof, and various changes in the invention may be made within the scope of the appended claims without departing from the spirit of the invention, and the scope thereof is determined by the claims which follow.

I claim:

1. A sharps disposal container for disposing of used pen syringe needles, comprising:

a) a substantially rigid receptacle defining an inner chamber for receiving sharps;

b) a cover secured to said receptacle and closing said inner chamber, said cover including means for providing access to said inner chamber;

c) a closure member pivotally connected to said cover, said closure member having a first position for sealingly engaging said access means and a second position for unsealing said access means; and d) latch means for locking said cover to said receptacle.

2. The container of claim 1 wherein said receptacle includes a flange spaced from and extending about the perimeter of said receptacle, said flange including an inwardly extending leg member securing said flange to said receptacle, said flange and said leg defining an open channel about the perimeter of said receptacle.

3. The container of claim 2 wherein said cover includes a downwardly extending rim received in said open channel upon assembly of said cover with said receptacle.

4. The container of claim 1 wherein said cover includes at least one bracket mounted on said cover, said bracket being adapted for pivotally securing an end of said closure member to said cover.

5. The container of claim I wherein said access means includes an upstanding cylinder projecting upward from a top surface of said cover and oppositely located truncated cone projecting downward from a bottom surface of said cover, said cylinder and said cone defining an axial passage opening into said inner chamber.

6. The container of claim 5 wherein said cone includes a plurality of longitudinally extending ridges disposed about the internal surface of said cone for firmly gripping a needle received through said axial passage.

7. The container of claim 5 wherein said closure member includes a cap adapted for sealing engagement with said cylinder, said cap including a plunger projecting downward from a bottom surface of said cap and having a vertical axis coincident with the vertical axis of said cap.

8. The container of claim 7 wherein said plunger includes a channel extending from a distal end of said plunger to a transverse shoulder inwardly spaced from said distal end of said plunger.

9. The container of claim 1 wherein said latch means includes a longitudinal tab extending from said closure member and being in axial alignment therewith, said tab including a notch formed by opposed angular surfaces extending from a bottom surface of said tab and joining at a point below a top surface of said tab, and further including a latch member projecting perpendicularly and inwardly from the distal end of said tab for interlocking engagement with said flange about the perimeter of said receptacle.

10. A method for disposal of used pen syringe needles, comprising the steps of:

a) unlatching a closure member pivotally mounted on a container enclosing an inner chamber;

b) lifting said closure member to expose an axial passage opening into said inner chamber;

c) inserting a needle and needle hub mounted on the barrel of a pen syringe into said axial passage until a forward end of the pen syringe barrel engages a circumferential shoulder extending horizontally into said axial passage;

d) gripping said needle hub and removing the needle from the pen syringe by twisting and unscrewing the pen syringe barrel from the needle and needle hub;

e) inserting said plunger into said axial passage into engagement with said needle hub and forcing said needle and needle hub through said axial passage into said inner chamber of said receptacle; and f) locking said closure member in sealing engagement with said axial passage.

* * * * *